United States Patent [19]
Cunningham-Rundles

[11] Patent Number: 5,169,627
[45] Date of Patent: Dec. 8, 1992

[54] ORAL PHARMACEUTICAL COMPOSITION CONTAINING A POLYETHYLENE GLYCOL-IMMUNOGLOBULIN G CONJUGATE FOR RECONSTITUTION OF SECRETORY IMMUNITY AND METHOD OF RECONSTITUTING SECRETORY IMMUNITY

[75] Inventor: Charlotte Cunningham-Rundles, New York, N.Y.

[73] Assignee: Mount Sinai School of Medicine of the City University of New York, New York, N.Y.

[21] Appl. No.: 783,360

[22] Filed: Oct. 28, 1991

[51] Int. Cl.$^5$ .................. A61K 39/395; A61K 39/44
[52] U.S. Cl. ................. 424/85.91; 424/85.8; 530/391.1; 530/406; 530/410
[58] Field of Search ............ 424/85.91, 85.8; 530/389, 406, 410, 520–589, 391.1

[56] References Cited
U.S. PATENT DOCUMENTS

| | | | |
|---|---|---|---|
| 4,179,337 | 12/1979 | Davis et al. | 530/406 X |
| 4,477,432 | 10/1984 | Hardie | 424/85.8 |
| 4,496,689 | 1/1985 | Mitra | 530/410 X |
| 4,714,612 | 12/1987 | Nakamura et al. | 424/85.8 |
| 4,732,863 | 3/1988 | Tomasi et al. | 530/387 X |

*Primary Examiner*—Howard E. Schain
*Attorney, Agent, or Firm*—Brumbaugh, Graves, Donohue & Raymond

[57] ABSTRACT

Polyethylene glycol serum immunoglobulin conjugates exhibit substantial resistance to degradation by intestinal enzyme while retaining their immuno-activity. Thus, PEG-IgG or PEG-IgA conjugates can be used as orally administered therapeutics to treat patients with gastrointestinal immunodeficiency to reconstitute secretory immunity. Preferred conjugates are made by reacting activated PEG and IgG in ratios of from 1:5 to 1:1000 such that less than about 27% of the IgG lysine residues are bonded to the PEG. The conjugates are advantageously formulated into a pharmaceutical composition comprising the conjugate and a pharmaceutically acceptable oral carrier. Particularly for administration to infants, a preferred oral carrier is milk.

16 Claims, 9 Drawing Sheets

ORAL PHARMACEUTICAL COMPOSITION CONTAINING A POLYETHYLENE GLYCOL-IMMUNOGLOBULIN G CONJUGATE FOR RECONSTITUTION OF SECRETORY IMMUNITY AND METHOD OF RECONSTITUTING SECRETORY IMMUNITY

BACKGROUND OF THE INVENTION

The present invention relates to an oral pharmaceutical composition containing a polyethylene glycol-immunoglobulin, particularly polyethylene glycol-immunoglobulin G (PEG-IgG) conjugate and to the oral administration of a PEG-Ig conjugate to patients with gastrointestinal secretory immunodeficiency to reconstitute secretory immunity.

The components of the gastrointestinal immune system consist of lymphoid tissues concentrated in Peyer's patches, intraepithelial lymphocytes, phagocytic cells, antibodies, and complement components. Secretory IgA is the major antibody in the gastrointestinal system. It differs from serum IgA by the presence of two additional polypeptide chains, a J chain and a secretory component. Because of this additional structure, secretory IgA resists proteolytic digestion.

Secretory immune deficiency is a commonly encountered disorder that arises from a variety of congenital, physiologic, or pathologic mechanisms. Infants normally have secretory IgA deficiency since IgA is produced in only very low amounts for the first few months of life. (This condition is remedied when the infants receive their mother's milk which contains secretory IgA.) Additionally, patients with selective IgA deficiency or common variable immunodeficiency also have a deficiency of IgA. Patients undergoing chemotherapy and radiation suffer the destruction of IgA producing plasma cells resulting in secondary secretory IgA deficiency. Further instances of acquired persistent secretory IgA deficiency occur, e.g., in bone marrow transplant recipients, and in acquired immunodeficiency due to HIV infection.

As is apparent from the effectiveness of mother's milk in overcoming secretory IgA deficiency in infants, oral administration of the antibody can provide therapeutic advantages. Human milk, and especially human colostrum, might provide the ideal form of immunoglobulin for oral use, but there are major difficulties in the procurement, preparation, sterilization, and standardization of this substance. In addition, there is the possibility that banked breast milk could transmit viral infections.

A few studies have been done to assess the oral use of commercially available pooled human serum immunoglobulin to reconstitute secretory immunity (see Table 1). While these studies report some success, the stability of serum immunoglobulin in the gastrointestinal tract is questionable because of proteolytic digestion of the unprotected serum immunoglobulins. Enzymes such as trypsin and pepsin attack serum immunoglobulins and render them ineffective against immunologically undesirable materials such as bacteria.

It is the object of the present invention to provide an oral pharmaceutical composition which can be made from pooled human serum immunoglobulin G or serum IgA that resists proteolytic digestion and thus a convenient means to reconstitute secretory immunity in patients with gastrointestinal immunodeficiency through the oral administration.

SUMMARY OF THE INVENTION

Conjugates coupling poly(n-vinylpyrrolidone), glucosides, albumin, polyvinyl alcohol, carboxymethyl cellulose, amino acid polymers, polyacrylic acid, polymaleic acid, or preferably polyethylene glycol with serum immunoglobulins, such as immunoglobulin G exhibit substantial resistance to degradation by intestinal enzymes while retaining their immuno-activity. Thus, these immunoglobulin conjugates can be used as orally administered therapeutics to treat patients with gastrointestinal immunodeficiency to reconstitute secretory immunity. Preferred conjugates containing IgG are made by reacting activated PEG and IgG in ratios of from 1:5 to 1:1000 such that less than about 27% of the IgG lysine residues are bonded to the PEG. The conjugates are advantageously formulated into a pharmaceutical composition comprising the conjugate and a pharmaceutically acceptable oral carrier. Particularly for administration to infants, a preferred oral carrier is milk, or milk formulae.

DESCRIPTION OF THE PREFERRED EMBODIMENT

Figure 1A:
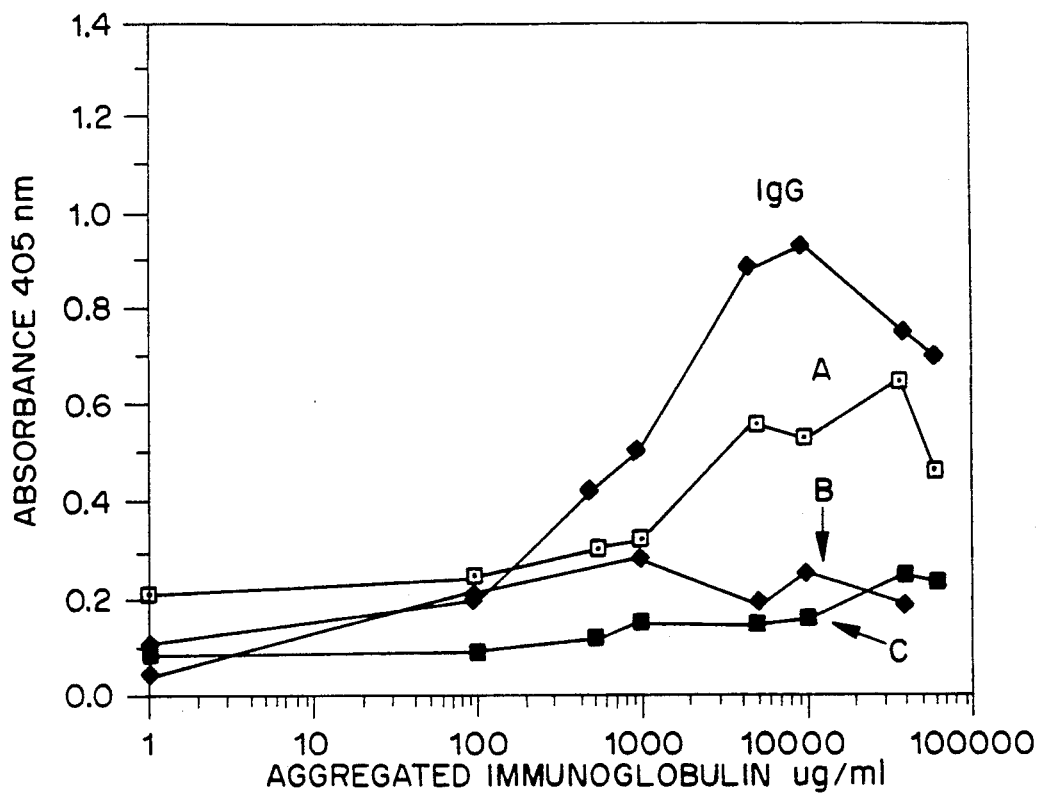
FIG. 1A - illustrates the reduced abilities of PEG conjugate A, B, and C to bind to microtiter plates coated with antibody to compliment component C3c as compared to native IgG.
Figure 1B:
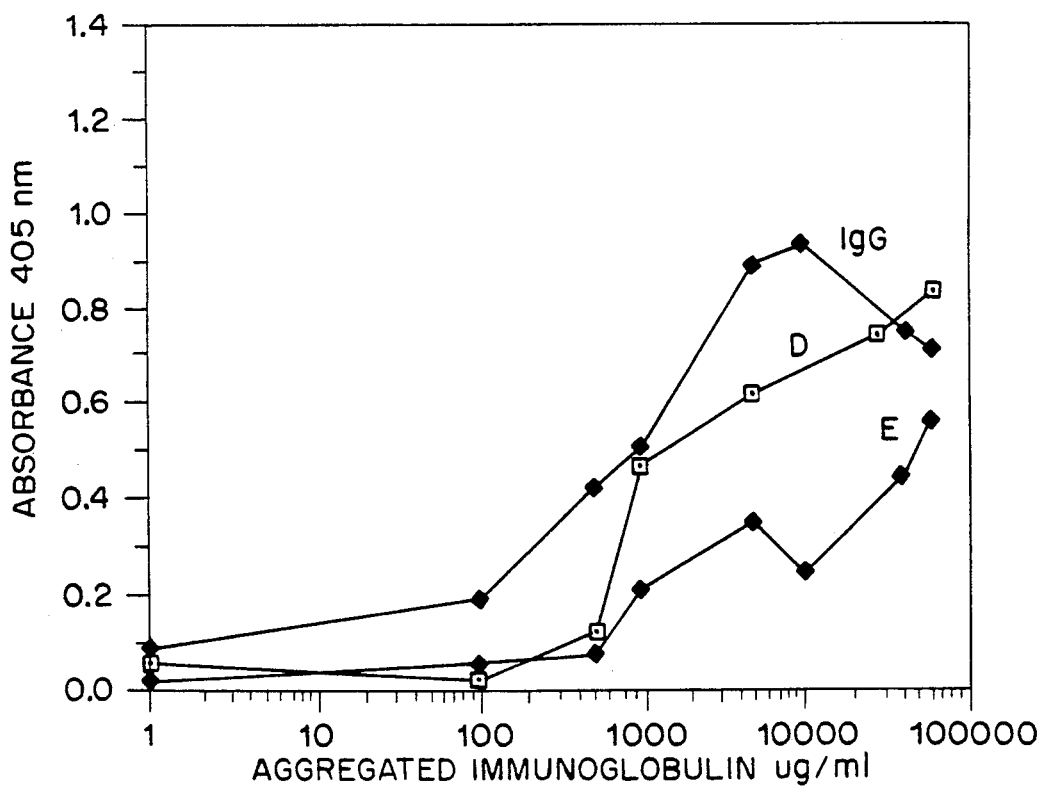
FIG. 1B - illustrates the reduced abilities of PEG conjugate D and E to bind to microtiter plates coated with antibody to complement component C3c, as compared to native IgG.
Figure 1C:
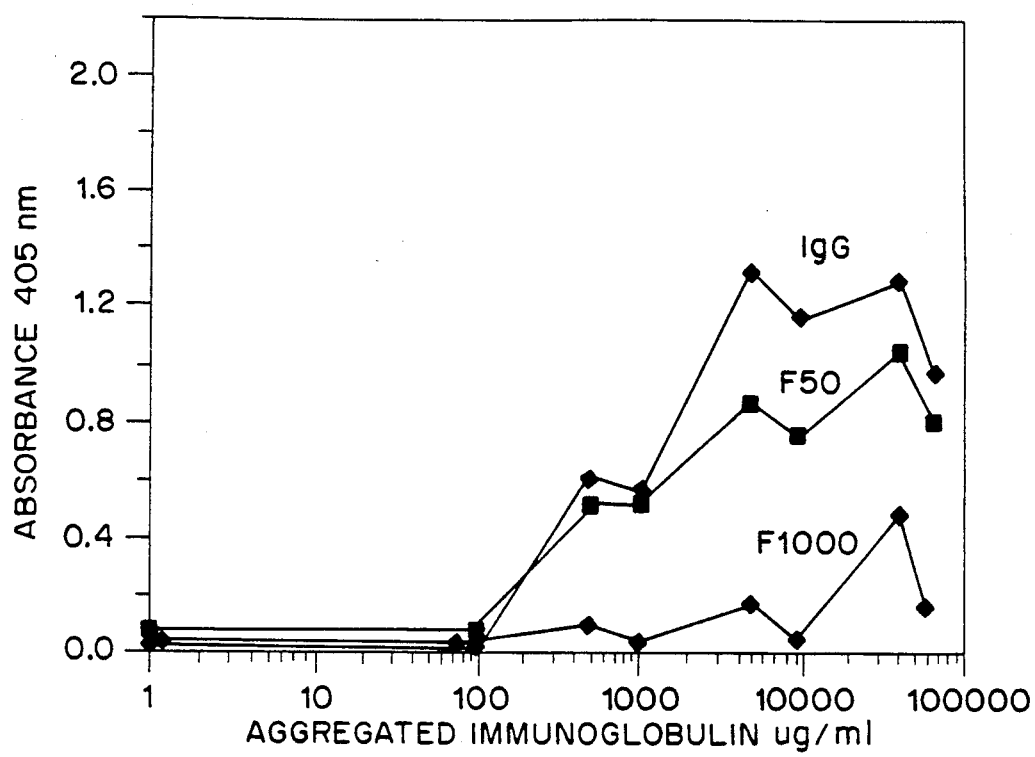
FIG. 1C - illustrates the reduced abilities of PEG conjugate F50 and F100 to bind to microtiter plates coated with antibody to complement component C3c, as compared to native IgG.
Figure 2A:
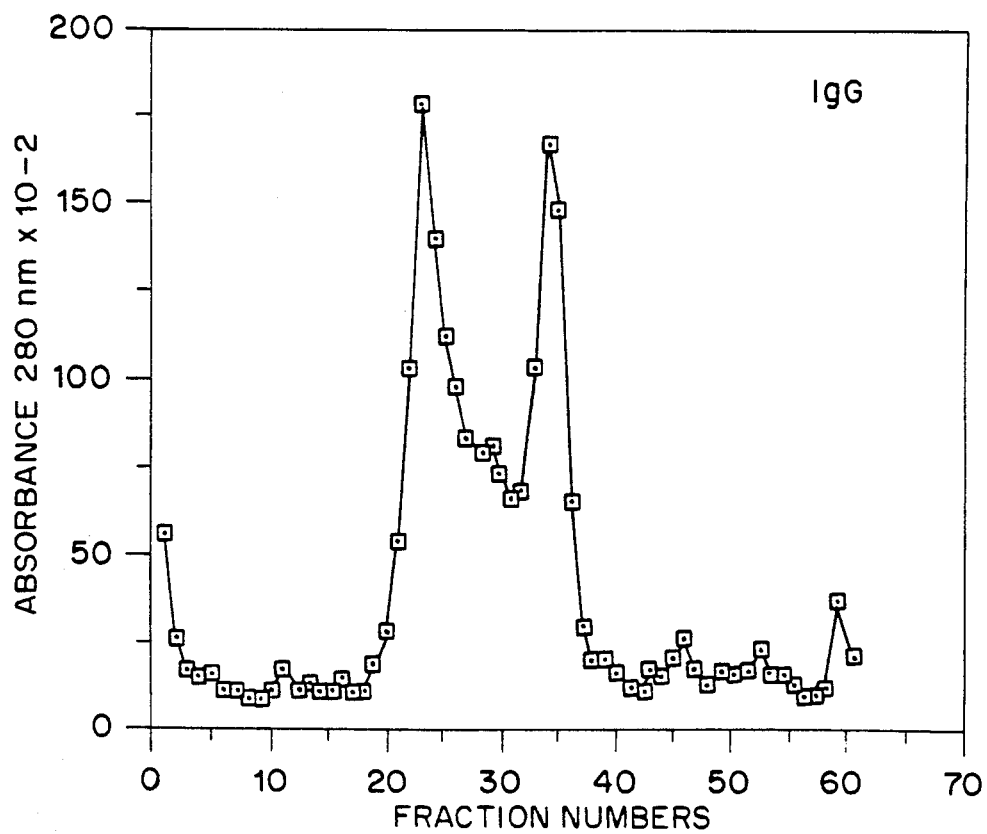
FIG. 2A - shows the susceptibility of unconjugated IgG to digestion by trypsin.
Figure 2B:
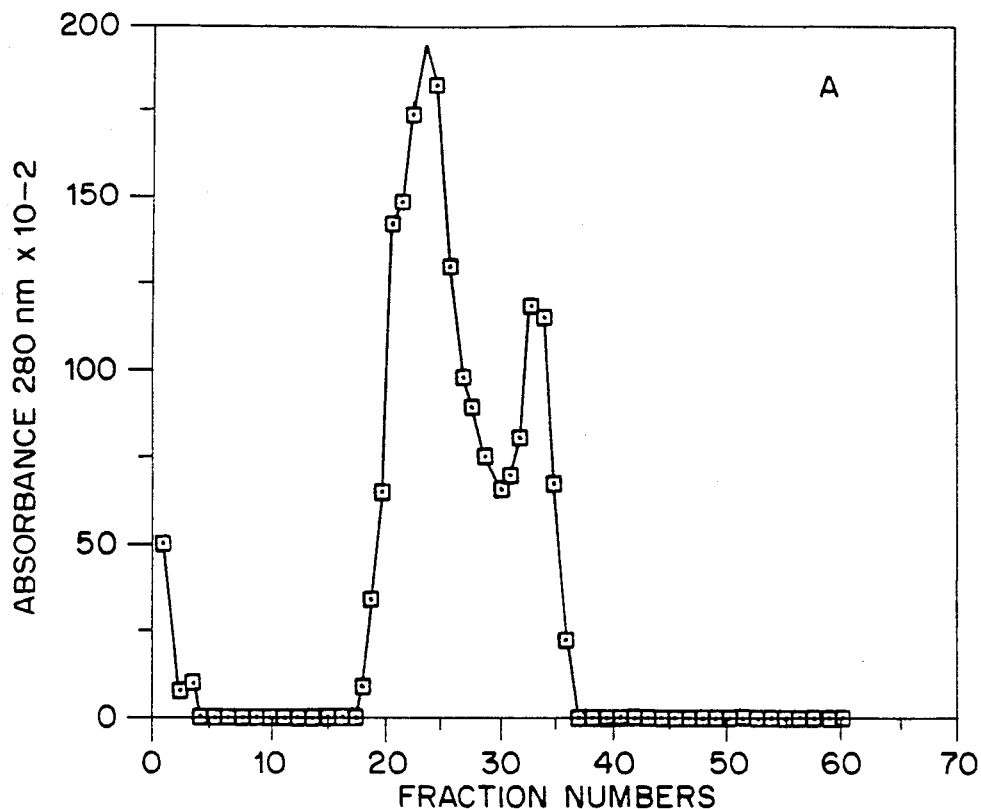
FIG. 2B - shows the reduced susceptibility of PEG-IgG conjugate A to digestion by trypsin.
Figure 2C:
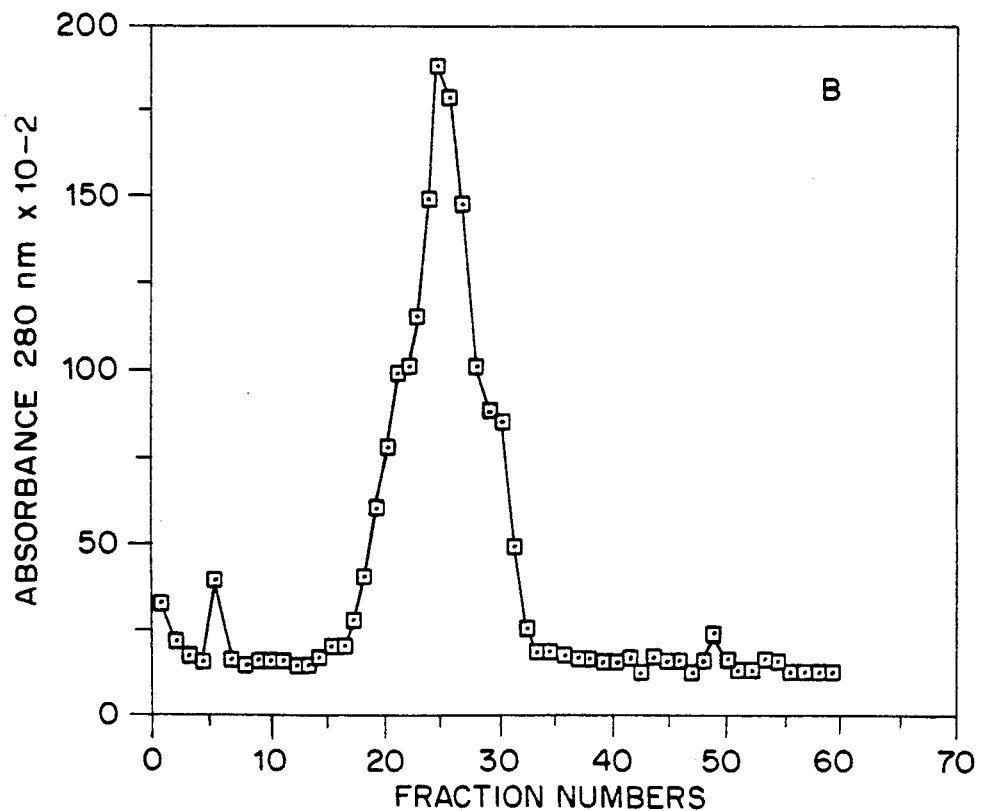
FIG. 2C - shows the lack of susceptibility of PEG-IgG conjugate B to digestion by trypsin.
Figure 2D:
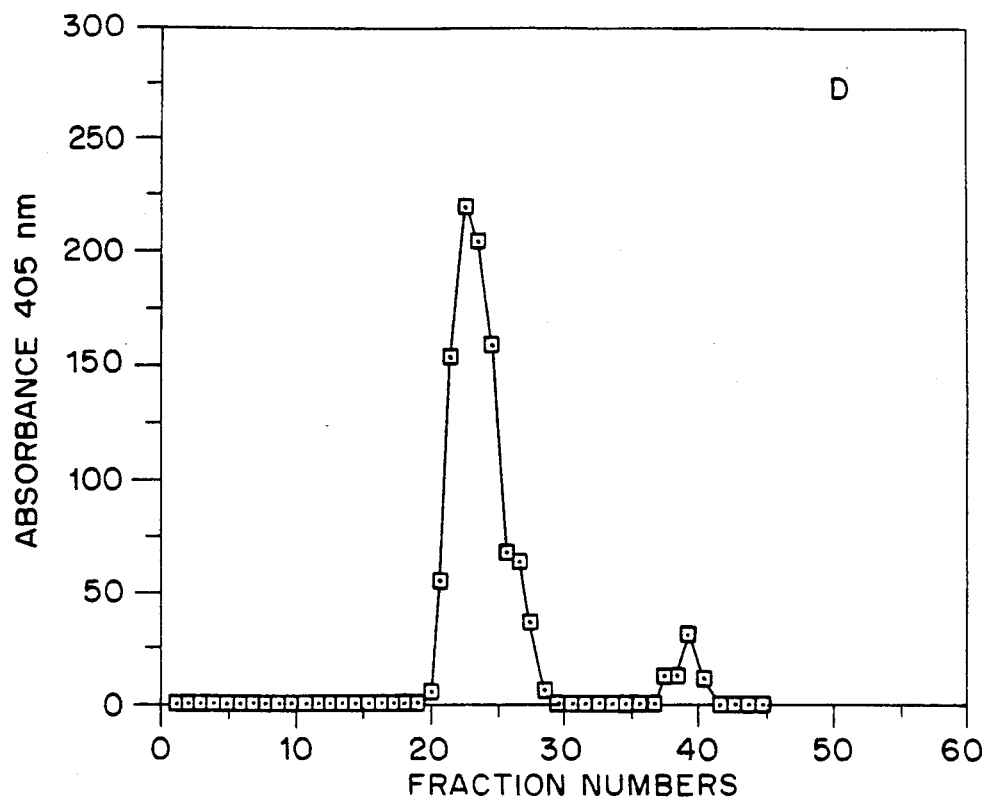
FIG. 2D - shows the lack of susceptibility of PEG-IgG conjugate D to digestion by trypsin.
Figure 2E:
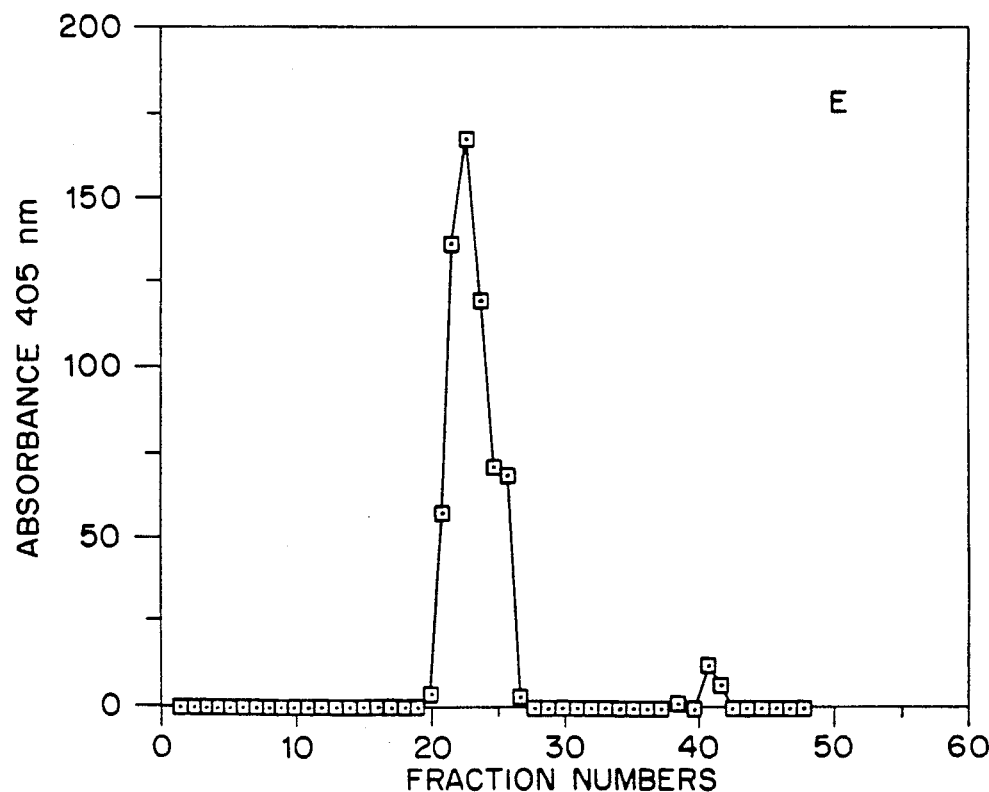
FIG. 2E - shows the lack of susceptibility of PEG-IgG conjugate to E to digestion by trypsin.
Figure 2F:
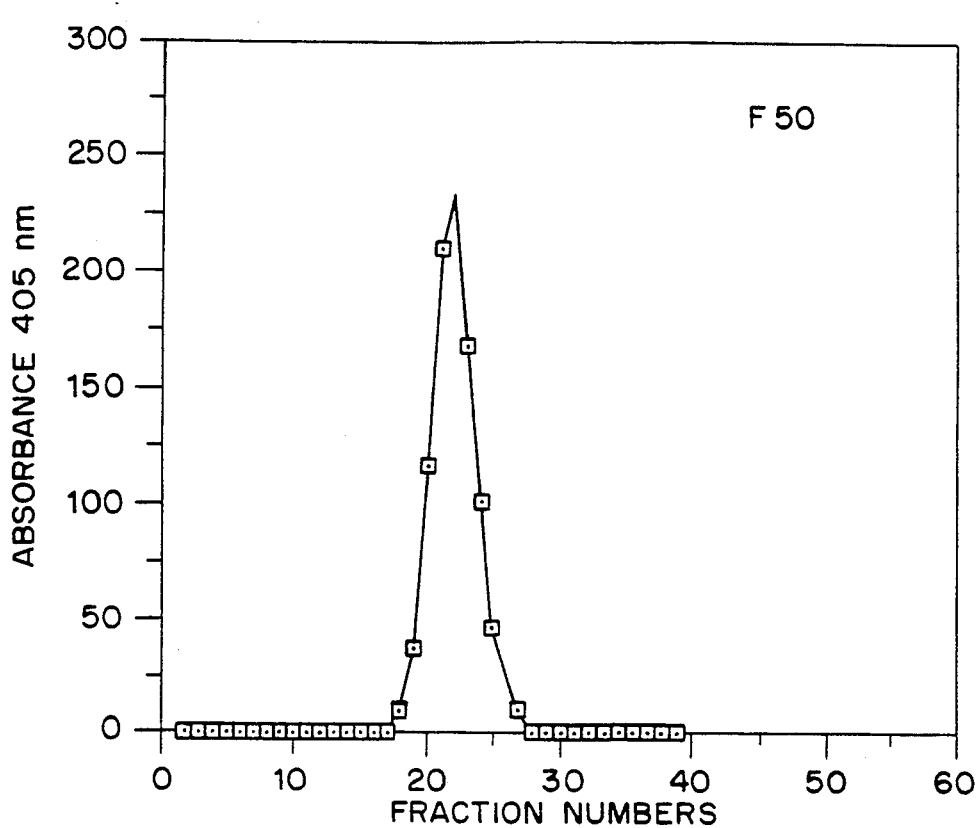
FIG. 2F - shows the lack of susceptibility of PEG-IgG conjugate to F50 to digestion by trypsin.
Figure 2G:
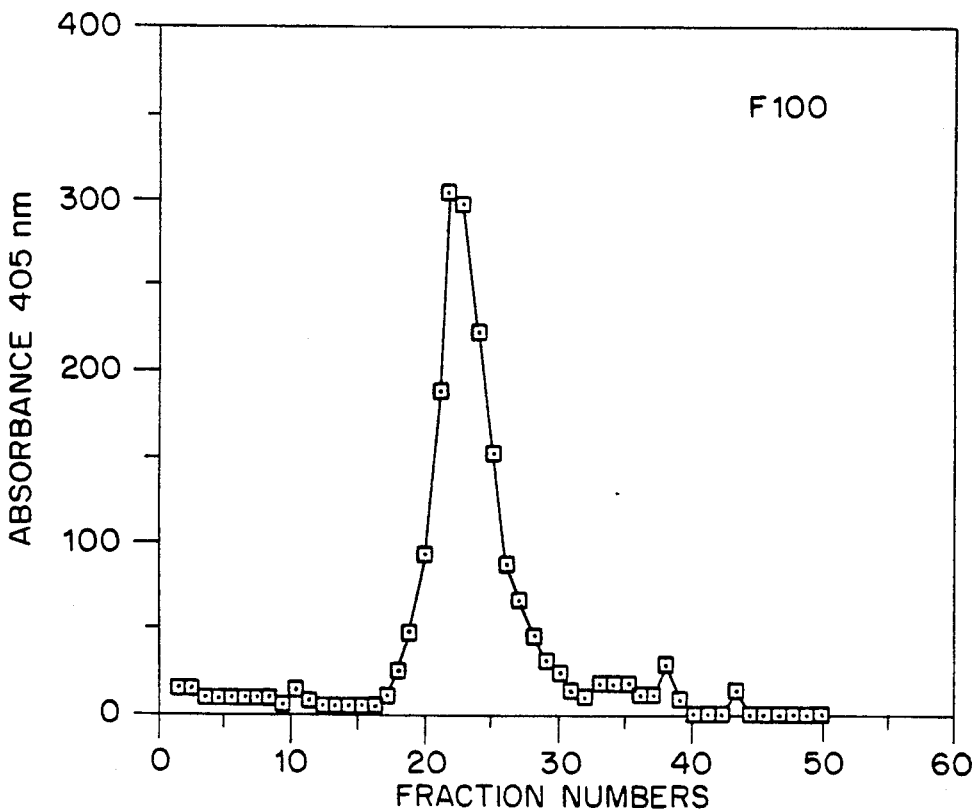
FIG. 2G - shows the lack of susceptibility of PEG-IgG conjugate to F100 to digestion by trypsin.
Figure 3A:
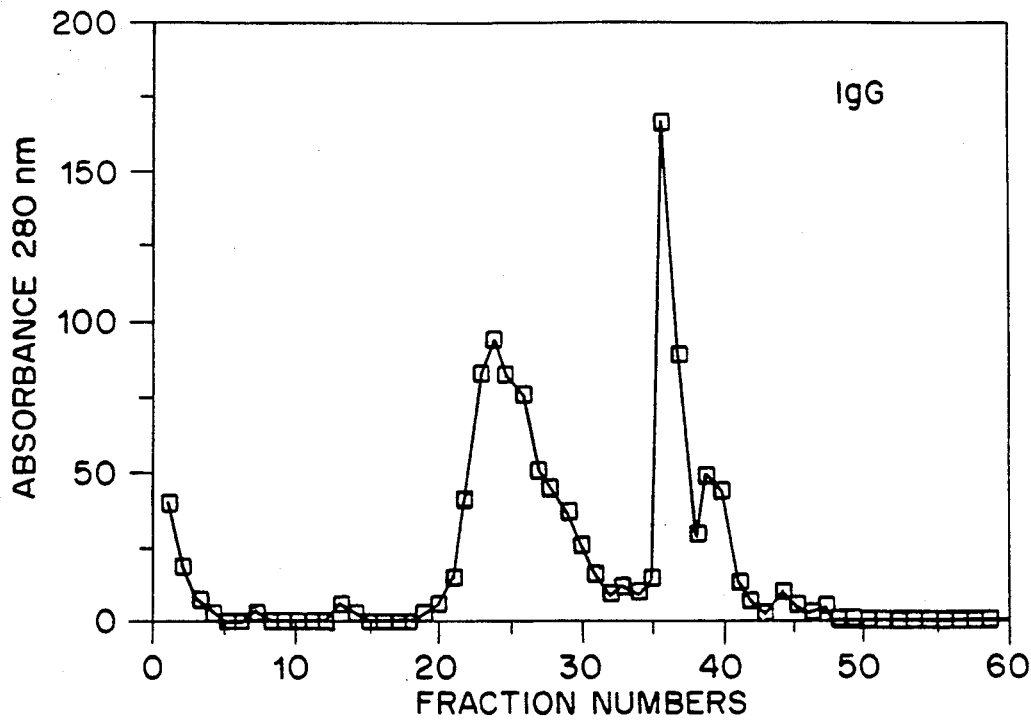
FIG. 3A - shows the susceptibility of unconjugated IgG to digestion with chymotrypsin.
Figure 3B:
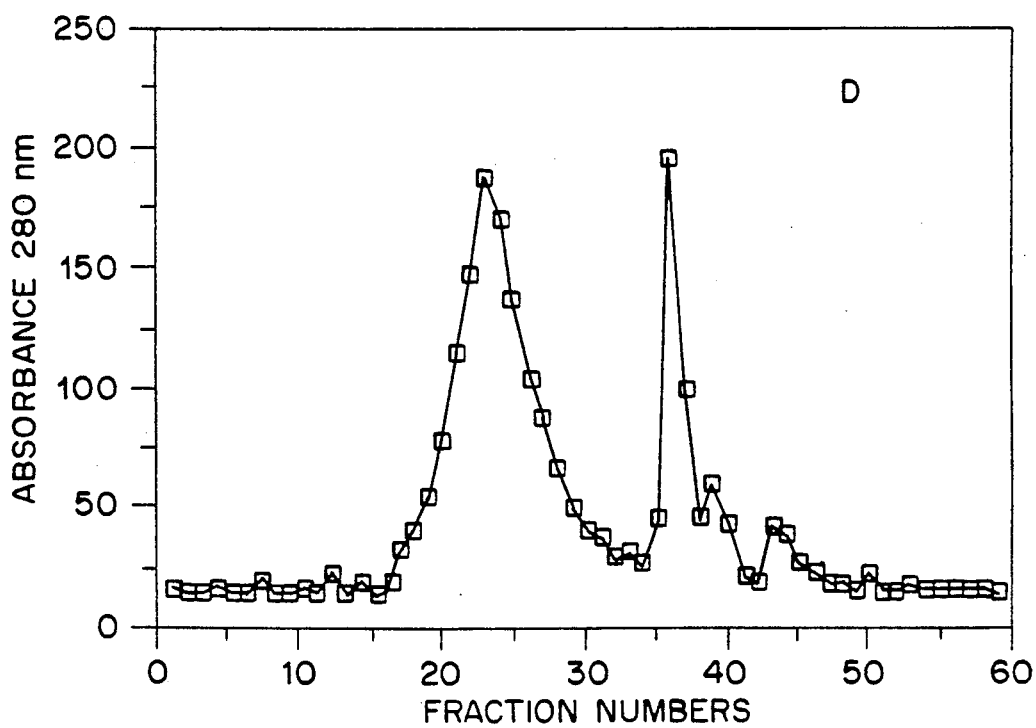
FIG. 3B - shows the reduced susceptibility of PEG-IgG conjugate D to chymotrypsin.
Figure 3C:
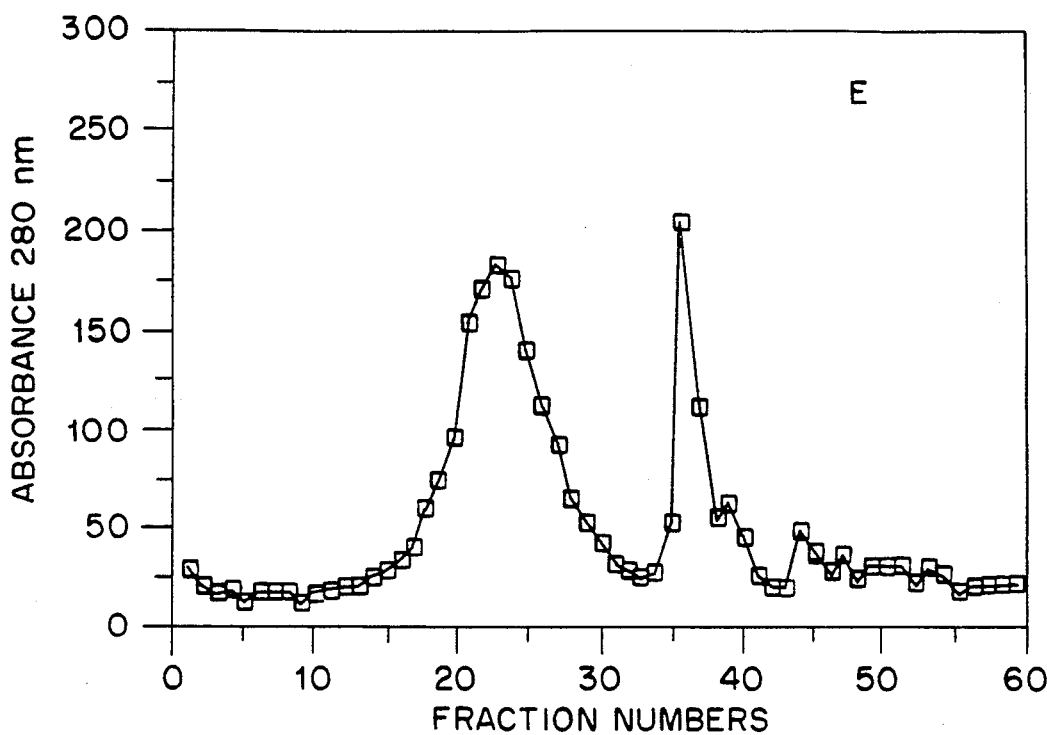
FIG. 3C - shows the reduced susceptibility of PEG-IgG conjugate E to chymotrypsin.
Figure 3D:
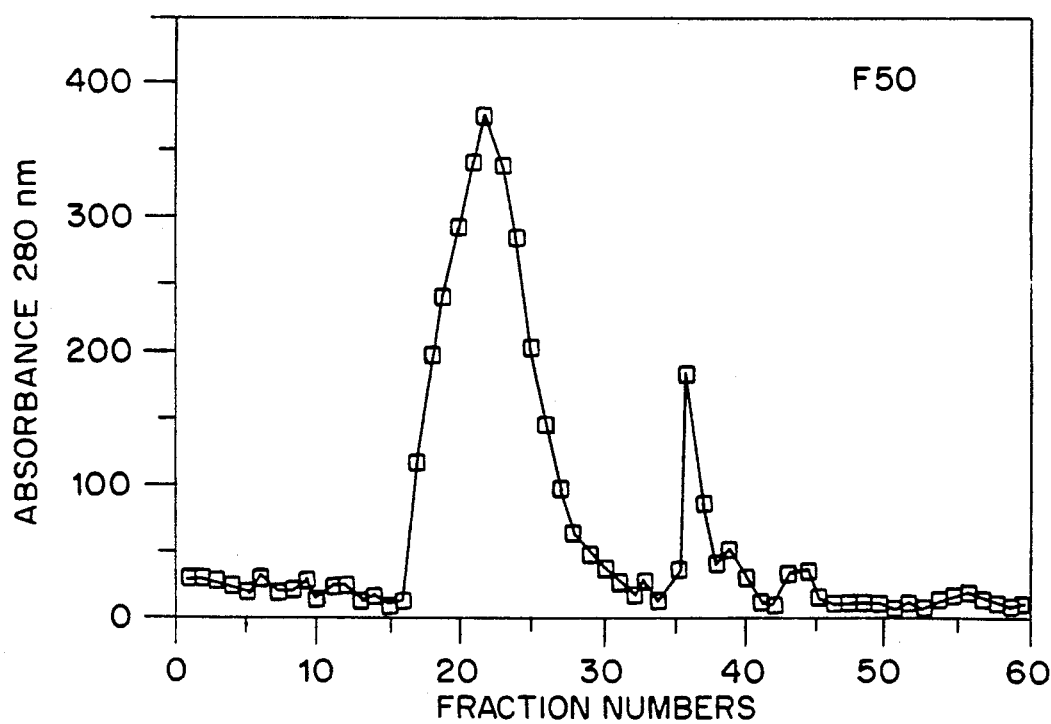
FIG. 3D - shows the reduced susceptibility of PEG-IgG conjugate F50 to chymotrypsin.
Figure 4A:
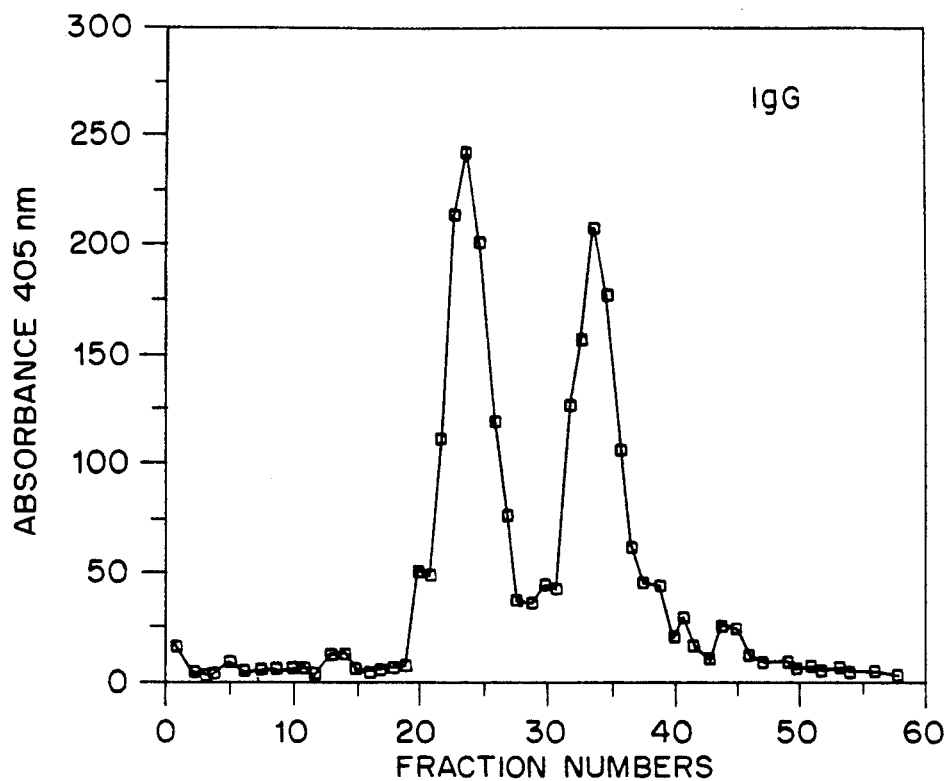
FIG. 4A - shows the susceptibility of native IgG to digestion by pepsin.
Figure 4B:
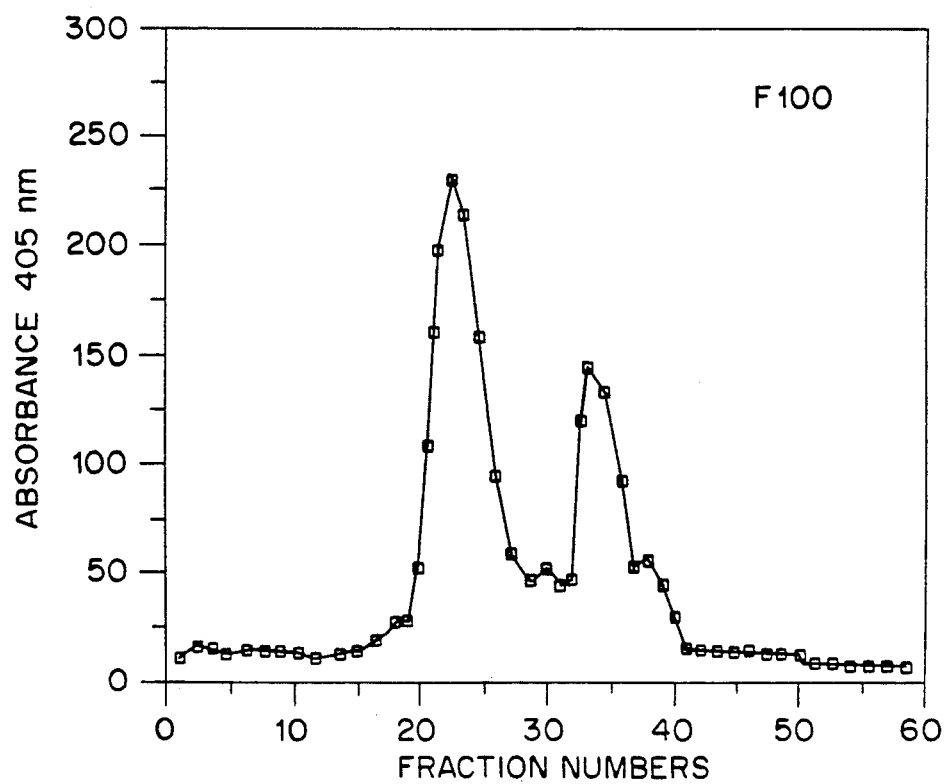
FIG. 4B - shows the reduced susceptibility of PEG-IgG conjugate F-100 to digestion by pepsin.
Figure 4C:
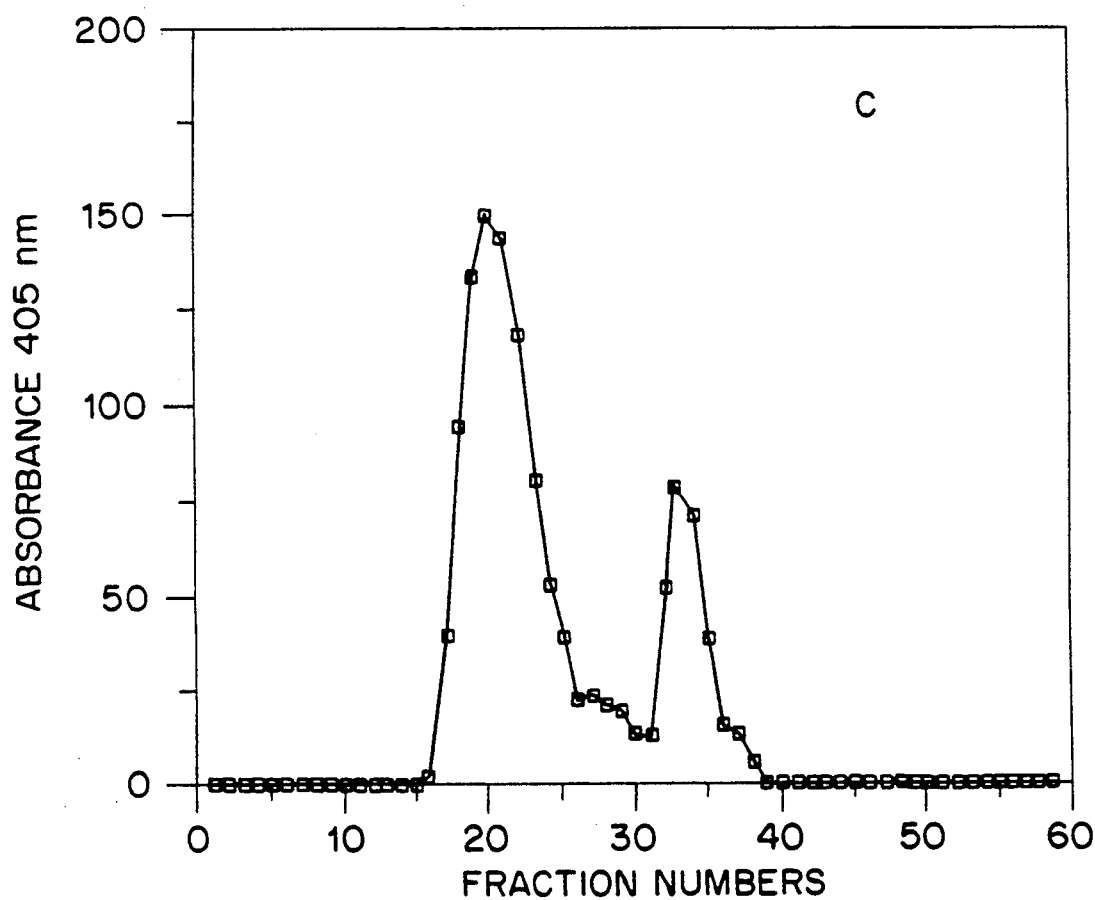
FIG. 4C - shows the reduced susceptibility of PEG-IgG conjugate C to digestion by pepsin.

As used herein, a polyethylene glycol-immunoglobulin conjugate is a serum immunoglobulin covalently bonded to polyethylene glycol through primary amines (amino terminus and lysine residues). In particular, the immunoglobulin in the conjugate may be serum IgG or serum IgA. These immunoglobulins may be recovered from samples of serum, but could be made synthetically if technology became available. Thus, the term "serum immunoglobulin" is intended to define the structure rather than a necessary source of the immunoglobulin portion of the conjugate.

The polyethylene glycol must be of sufficient size to impart protection to the immunoglobulin without significantly impairing activity. PEG's with molecular weights of from about 2000 to about 8000 are suitably used.

Such Ig-PEG conjugates are immunologically active but have greater resistance to proteolytic enzymes and thus can be used orally for reconstitution of secretory immunity.

PEG-IgG conjugates can be produced by at least three methods involving different chemical methods of attachments of immunoglobulin molecules to PEG. The molar ratio of PEG : immunoglobulin may vary from about 1:1 to 1:1000, depending on the method employed. PEG-Ig (either IgG or IgA) conjugates for use in the invention can be formed from concentrated Ig obtained from human serum. Serum immunoglobulin is dissolved in a basic buffer solution, for example 0.01M sodium phosphate buffer, pH 7.8, and then dialyzed against the buffer to remove residual salts. The concentrated serum Ig is then combined with activated PEG which can be obtained by a chemical process involving either 1,1,'-carbonyldiimidazole, or cyanuric chloride or succinylsuccinamide to form the conjugate.

PEG-Ig conjugates produced using PEG activated by 1,1'- carbonyldiimidazole exhibits antigen binding capacity substantially equivalent to that of native IgG. The immunoglobulin G contained in PEG-IgG conjugates are fully capable of binding a spectrum of proteins or viruses. The use of PEG activated by succinylsuccinamide, provides Ig conjugates with similarly broad binding characteristics. However, use of the cyanuric chloride activation method produces some loss of antibody binding capacity at coupling ratios as low as 1:100. At a ratio of 1:288, antibody binding activity is lost. This is in agreement with the published observation of loss of antibody binding activity at a coupling ratio of 1:1000. Ling et al., J. of Immunological Methods, 59 : 327-337 (1983).

PEG-IgG conjugates are also rendered relatively impervious to enzymatic cleavage by trypsin, chymotrypsin and pepsin. The mechanism of the increased resistance to trypsin is understandable in view of the fact that PEG binds predominantly to lysine residues on the immunoglobulin molecules and that trypsin cleaves peptide bonds contributed by lysine or arginine residues. Blockage of a proportion of lysine residues by PEG is apparently sufficient to inhibit trypsin activity almost completely. PEG-Ig conjugates are also less susceptible to the action of chymotrypsin; chymotrypsin cleaves at peptide bonds adjacent to tyrosine, tryptophan and phenylalanine; thus steric hinderance by attached PEG molecules is the probable mechanism. As to pepsin, since pepsin cleaves at defined regions in the hinge region of IgG molecules, the resistance of PEG-Ig conjugates to pepsin cleavage is likely due to stearic hinderance by the bonded PEG residues near the hinge region.

The resulting PEG-Ig conjugates have properties which therefore closely mimic those of natural secretory IgA, and are suitable for oral administration to reconstitute secretory immunity in patients with gastrointestinal IgA immunodeficiency. Like secretory IgA, the PEG-Ig conjugate is able to withstand proteolytic cleavage by enzymes present in the gastrointestinal tract. Also PEG-Ig conjugates, like secretory IgA, are capable of binding antigens efficiently. Additionally, PEG-IgG conjugates fix complement less well than native IgG and exhibit decreased binding to Fc receptors. Secretory IgA binds to Fc receptors present mainly on granulocytes and monocytes, cells not normally found in the gastrointestinal lumen. These similarities in properties help the PEG-Ig conjugate assume the role of secretory IgA in the gastrointestinal tract, i.e., that of a "discreet housekeeper." PEG-Ig conjugates, like IgA, can thus provide efficient antigen binding but since complement fixation and binding to cells are restricted there should little local inflammation or other immune activation triggered.

These properties make PEG-IgG or IgA conjugates useful in the treatment of humans with secretory IgA deficiency. These immunologically compromised patients include infants in their first few months of life, patients with selective IgA deficiency or common variable immunodeficiency, immunologically compromised patients with secondary IgA gastrointestinal immunodeficiency as a result of chemotherapy or radiation; and patients with acquired persistent secretory IgA deficiency as a result of bone marrow transplants or HIV infection. Such patients may be helped by the oral administration of effective amounts of the PEG-immunoglobulin conjugates. In particular, administration of from 50mg/kg body weight 2 times a day to 100 mg/kg 4 times a day should provide useful therapeutic results.

For use as an orally administered therapeutic, PEG-IgG conjugates are advantageously formulated as an oral pharmaceutical composition comprising the conjugate and an oral carrier. In such a composition, the oral carrier may be conventional excipients used in making tablets (e.g. lactose) or a controlled release or protective (e.g. enteric) coating systems. The oral carrier may also be an aqueous liquid carrier containing at least one flavoring component. Preferred liquid carriers (including flavoring components), especially for treatment of infants, are milk, milk substitutes (formula) and fruit juices, although liquid compositions containing artificial flavorants or sweeteners or natural flavor extracts may also be used.

EXAMPLE 1

Serum immunoglobulin G preparations were formed by dissolving serum immunoglobulin G in 0.01 M sodium phosphate buffer at pH 7.8. The resulting solution was then dialyzed against the buffer to remove residual salts. Determination of the final concentration of the immunoglobulin G was done spectrophotometrically using an extinction coefficient of 138 as $E1\%/280$ nm for IgG. See, Putnam F. W. in the Plasma Proteins, Putnam F. W., ed., Academic Press 1975 p.62.

EXAMPLE 2

Activation of polyethylene glycol (Sigma Chemical Co., St. Louis, Mo.) by 1,1'-carbonyldiimidazole was carried out in accordance with the method of Beauchamp et al., Analytical Biochem 131:25-33 (1983) by first dissolving polyethylene glycol (PEG) 2,000 or 8,000 in dioxane at 37° to provide concentration of 50 mM. Then 1,1'-carbonyldiimidazole (Sigma) was added to a final concentration of 500 mM. The PEG and 1,1'-carbonyldiimidozole solution was incubated with stirring at 37° C. for two hours to yield activated PEG. The activated PEG mixture was dialyzed extensively against phosphate buffered saline (PBS) in an Amicon cell using a 76 mm Diaflo Ultra Filtration membrane (XM 50) to remove residual carbonyldiimidazole. The resulting activated PEG solution was dialyzed against distilled water, lyophilized, and stored desiccated.

EXAMPLE 3

Activated PEG produced by the method in example 2 was dissolved in 0.01 mM sodium borate buffer, pH 8.5, with various concentrations of serum immunoglobulins, to provide PEG-IgG conjugates with molar ratios of 1:5 to 1:1000 at 4° for 96 hours. These solutions were then concentrated as needed to assess biologic activities by lyophilization or by pressure dialysis in the Amicon cell.

EXAMPLE 4

Activation of polyethylene glycol was also accomplished using the method of Abuchowski et al., J. Biol. Chem. 252:3578-3581, 1977, by dissolving 5.5 g cyanuric chloride in 400 ml of anhydrous benzene containing 10 g anhydrous sodium carbonate. PEG 2000 or 8000 (19 g) was added and the mixture stirred for 16 hours at room temperature. The solution was filtered and 600 ml of petroleum ether added to the liquid and the precipitate collected. The precipitate (activated PEG) was redissolved in benzene and reformed in petroleum ether twice more.

EXAMPLE 5

To form PEG-IgG conjugates, activated PEG prepared in accordance with Example 4 was added to IgG in 0.1M borate buffer at pH 9.2 at PEG:IgG molar ratios of 1:5 to 1:500. The mixture was incubated at 4° C. for 1 using a 76mm Diaflo Ultrafiltration membrane (PM10) in Amicon cell using 0.01M phosphate buffer pH 7.3 as the dialyzing solution.

EXAMPLE 6

A third method of activating polyethylene glycol according to Joseph M., and Luisi PL., (Makromol. Biochem Biophys 7:175- 1984) is by using succinic anhydride to activate methoxypolyethylene glycol as follows. 50 grams of PEG are dissolved in 250 ml of a 1, 2 -dichoroethane solution containing 5 g succinic anhydride and 4 ml pyridine. After 3 days of reflux under nitrogen, the solution is filtered, the solvent evaporated, and the residue dissolved in 100 ml water. This residue is washed twice with 50 ml diethyl ether, and the PEG-succinate is extracted from the water phase and washed with two 50 ml of chloroform. After evaporation of the chloroform, about 43 grams of PEG-succinate is obtained.

The PEG-succinate is dissolved according to the method described by Anderson et al , J. Am Chem Soc 86:1839, 1964), and adapted by Abuchowski et al., in 200 ml dimethylformamide at 37° and N-hydroxy succinimide (10% molar excess) is added. The solution is cooled to 0°, and an amount of dicyclohexyl carbodiimide, equal in molar quantity to N-hydroxysuccinamide is dissolved in 10 ml dimethylformamide and added dropwise with continuous stirring. The mixture is left at room temperature for 24 hours and filtered. One hundred ml of cold benzene is added, and methoxypolyethylene glycol succinimidyl succinate (SS-PEG) is precipitated by the dropwise addition of 200 ml petroleum ether at 0°. The precipitate is collected on a sintered glass filter. Dissolution in benzene and precipitation with petroleum ether is repeated three times. SS-PEG is stored in a desiccator at −20° C.

EXAMPLE 7

PEG-immunoglobulins are prepared by the following procedure. Fifteen grams of SS-PEG prepared according to example 6 is added to 100-1000 mg of immunoglobulin in 100 ml 0.05 M phosphate buffer, 0.85% NaCl, pH 7.2 (PBS) 15 g SS-PEG. The mixture is stirred for 30 min at room temperature and clarified by Millipore filtration (1.2 $\mu$m membrane). Unbound SS-PEG is removed by dialysis against 10 volumes of buffer using an Amicon cell as described above. Each preparation of PEG-IgG is sterilized by filtration and stored at 4° C.

EXAMPLE 8

Various PEG IgG conjugates were produced, having molar ratios of 1:5 to 1:1000. To determine the degree of conjugation which resulted, the degree of substitution of primary amines was determined. To do this, the amount of florescence produced by coupling an o-pthalaldehyde reagent (Fluoraldehyde, Pierce, Rockford, Ill.) to available primary amines was measured. For this IgG-PEG conjugates or unmodified IgG were diluted to concentrations of 50, 25, 12.5 and 6.25 $\mu$g/ml in PBS. To determine the IgG concentrations of these preparations, ultraviolet absorption method, with spectrophotometric reading at 280 nm could be used since PEG has no absorbance at this wavelength. To 100 $\mu$l aliquots of these solutions in Micro Fluor microtiter plates (DynaTech Laboratories, Inc., Alexandria Va.), 100 $\mu$l of Fluoraldehyde was added. After 10 minutes the results were read in a Micro Fluor Reader (DynaTech). Considering unmodified IgG as 100% fluorescence, the degree of fluorescence of each conjugate was determined; from this, the percentage of binding of PEG to primary amines could be calculated. Since activated PEG binds mostly to primary amines (N-terminus and lysine residues) by either method of activation, loss of fluorescence is proportional to the amount of PEG coupled. Table 2 gives the coupling ratios used and the percentage of primary amines coupled using both procedures.

EXAMPLE 9

Preservation of antibody binding was tested by comparing the antibody binding capacities of the PEG-IgG conjugate to a similar concentration of IgG which had not been modified. Antibody binding of PEG-IgG conjugates was determined by ELISA. For this, 100 $\mu$l of 10$\mu$g/ml of various protein of microbial antigens in 0.1M Na carbonate buffer pH 9.6, were used to coat wells of microtiter plates (NUNC, Maxisorb, Vangard International, N.Y.). The antigens used were egg albumin (3x crystallized Sigma), bovine casein (Sigma), bovine immunoglobulin (Sigma), tetanus toxoid (Wyeth-Ayerst Laboratories) and mumps antigen (Merck Sharps and Dohme). Antibodies to mumps, cytomegalovirus, toxoplasmosis, rubella, herpes simplex, and herpes zoster were also determined by ELISA using a standard commercial kit (Diamedix, Miami Fl). To test conjugates, PEG-IgG conjugates or for comparison, unmodified IgG, were diluted to supply 0.1 mg/ml in PBS-containing Tween 0.1% (Sigma). 100 μl aliquots of these solutions were added to antigen-coated wells, previously well washed with normal saline containing Tween 0.1%. After 3 hours at 37° C. (or overnight at 4° C.), wells were washed again and 100 μl of goat anti-human IgG alkaline phosphatase conjugate (Tago, Burlingame Calif.) diluted 1:1000 in PBS-Tween was added to each well. These wells were incubated at 37° C. for 3 hours washed, and a substrate solution (nitrophenyl phosphate (NPP), 1 mg/ml in 0.1M Tris HCl containing also 0.001M MgCl) was added. The resulting solution was then read in a Multiscan Titertek microtiter plate reader (Flow Laboratories, McLean, Va.).

Table 3 shows data for conjugates tested against the protein antigens, tetanus, chicken ovalbumin, mumps, bovine immunoglobulin and bovine casein. Overall, PEG IgG conjugates A to L were capable of binding to the antigen coated plates, although some conjugates had reduced binding capacities for a few antigens, as compared to native IgG. Conjugate F50, for example, had somewhat reduced binding for tetanus toxoid, and conjugates K and L had reduced binding to casein, and conjugate C, had reduced binding to all antigens. It appears that immunologic activity is retained when up to about 27% of the free lysines are coupled to the PEG. Conjugate I (cyanuric chloride activated; 1:288 coupling ratio) had essentially lost the ability to bind to any antigen coated plate.

Similarly, preparations A to L were quite capable of binding to the various protein antigens tested in a standard kit ELISA, with all of these conjugates being found to contain protective amounts of antibody when judged by a standard known positive IgG sample, and the provided plate controls. Again, conjugate I (1:288 motor ratio of coupling) was inactive. (Table 4).

EXAMPLE 10

To test if the PEG-IgG conjugates could bind to Fc receptors, the conjugates were heat aggregated and then tested for binding to U937, a macrophage cell line bearing abundant Fc receptors for IgG. Heat aggregated human IgG and PEG-conjugates were produced by heating 10 mg/ml solutions of each in PBS to 63° for 30 minutes. After removing the largest (visible) aggregates by brief centrifugation (3,000 rpm from 5 minutes) the aggregates contained in the supernatants of these solutions were used to test for binding to human Fc receptors present on the macrophage cell line U937. These cells (a gift of Dr. K. Sperber) were maintained in medium containing RPMI 1640 (GIBCO, Grand Island, N.Y.) containing 10% fetal calf serum, 10 mM glutamine, penicillin and streptomycin at 37° C. in a 5% $CO_2$ incubator. Two hundred μl of 3x washed $5 \times 10^6$ cells/ml in PBS containing 2% BSA and 0.1% Tween 20 were incubated with 10 or 50 μl of aggregated IgG or PEG-IgG conjugates at 37° C. for 30 minutes and then at 4° C. for 30 minutes. Cells were then gently washed 3 times in 2% BSA/PBS-Tween, and 25 μl fluorescein conjugated F(ab)'$_2$ goat anti human IgG (Tago) was added to each tube. After incubation at 4° C. for 45 minutes the cells were rewashed, and the degree of fluorescence for each aliquot determined by flow cytometer (FACS/IV, Becton-Dickenson Mountain View Calif.)

Table 5 shows the results obtained. The PEG-IgG conjugates did bind to U937, but with decreasing fluorescence being detected for immunoglobulins bearing increased amounts of PEG.

EXAMPLE 11

To determine if PEG-conjugates could fix complement component C3, two methods were used. In the first, heat aggregated conjugates were tested in comparison to heat aggregated IgG for their ability to bind to microtiter plates coated with polyclonal anti C3c or C3d antibodies (Dako, Accurate Chem. Westbury, N.Y.). For this, microtiter plates were coated with rabbit anti human C3c or C3d, at 20 μg/ml in 0.1M Na carbonate buffer, pH 9.6, at 4° C. for 16 hours. 100 μl of variously diluted aliquots of heat aggregated PEG IgG conjugated or non-conjugated IgG (providing 1 ng to 100 μg/ml IgG) were incubated with a standard amount of fresh normal serum (as a source of C3). After incubation at 37° for 3 hours, the wells were rewashed, and goat anti human IgG-alkaline phosphatase conjugate was added. After the addition of the NPP solution the resulting absorbance at 405 nm was subsequently determined. This test showed that as increasing amounts of PEG were bound to the IgG fraction, reduced amounts of IgG were detected on the coated microtiter plates. (FIGS. 1A, B and C.)

In the second method, immune complexes were formed by mixing PEG-IgG or native IgG at 225 μg/ml 22.5 μg/ml or 2.25 μg/ml with bovine κ-casein at a 2.5:1 molar ration in 50 μl PBS. PBS-0.1% Tween was added to bring the volume to 350 μl, and 350 μl of fresh normal human serum with no κ-casein binding antibody was added, incubation was continued for 3 hours at 37° C. Then, after washing, goat anti-mouse IgG-alkaline phosphatase conjugate was added (1:1500 in PBS-Tween), and the incubation continued for 3 hours at 37° C. Then the plates were washed and developed with NPP as usual.

At the three concentrations of immunoglobulins tested, more IgG-κ-casein immune complex, exposed to normal human serum, could bind to microtiter plates than could immune complexes formed using PEG-IgG. Table 6 shows data for one concentration (22.5 μg/ml). PEG IgG binding ranged from 42.0 to 79.6 percent of that found for native IgG.

EXAMPLE 12

Since in several of the above methods the binding of a second antibody to PEG-IgG conjugates to determine the biologic activities of these conjugates was used to compare PEG-IgG conjugates to native IgG, experiments to determine the relative binding of a second antibody to these conjugates in comparison to native IgG, were performed.

The assays used to determine the biologic activities of the PEG-IgG conjugates in comparison to native IgG depend upon the detection of IgG by a second, or sandwiching antibody conjugated to alkaline phosphatase or labeled with fluorescein. To interpret these experiments, it was necessary to determine if the PEG-IgG conjugate could be detected to the same degree as native IgG. To ascertain this, two methods were used. In the first, PEG-IgG conjugates or native IgG were diluted to a concentration of 10 μg/ml (by Absorbance at 280 nm) in 0.1M sodium carbonate buffer pH 9.8 and used to coat microtiter plates at 37° C. for 3 hours. After washing, alkaline phosphatase goat anti-human IgG (Tago) was added to each well, and after further incubation at 37° C. for 3 hours, the wells were washed and NPP added. The plates were then read as usual.

In the second assay, PEG-IgG conjugates and native IgG were diluted to 0.5 mg/dl in PBS, and tested by standard nephelometer methods using a Beckman Array Protein System, Brea, Calif. and a polyclonal goat anti human IgG (Beckman), to determine the IgG concentration by reference to an IgG standard curve.

Table 7 shows the binding of alkaline phosphatase labeled goat anti human IgG to PEG-IgG conjugates coated to wells of microtiter plates and the binding of an unlabeled goat anti human IgG for detection by nephelometer. Some degree of impairment of binding of these second antibodies was found for conjugates B, C, and F1000 when these were used to coat microtiter plates. When the same conjugates were tested in solution, only conjugate C showed significantly reduced binding by the second antibody. Thus, for all experiments conducted in solution, the testing of conjugates by use of a second antibody, was found to be justified—except for conjugate C which is poorly detected in this system.

EXAMPLE 13

A main goal of the invention was to provide an immunologically active IgG tested to render IgG resistant to enzyme cleavage. To test whether this goal is met, solutions of IgG or various PEG-IgG conjugates were exposed to trypsin, chymotrypsin or pepsin; the degree of fragmentation of IgG was then assessed by high pressure liquid chromatography.

Trypsin: Samples of IgG-PEG conjugates or unmodified IgG (15 mg/ml) were incubated with trypsin (Type III, Sigma) 1:100) at 37° C. for 3 hours in 0.05M Tris HCl buffer, pH 8.0. After this, a 4 fold excess of soybean trypsin inhibitor (Sigma) was added. Samples were frozen at −70° C. until analysis.

2. Chymotrypsin: Samples of native IgG and PEG-IgG conjugates (4.5 mg/ml in 0.2 M phosphate buffer Ph 7.0) were also digested with chymotrypsin (Sigma Type III, TLCK treated, 54 units per mg) at an enzyme to substrate ratio of 1:200. These samples were incubated at room temperature for 8 hours, and then the reaction was terminated by reducing the pH to 2.0 by 6N HCL. Samples were then frozen at −70° C. prior to analysis by HPLC.

3. Pepsin: IgG-PEG or unmodified IgG samples were incubated at 37° C. at 10 mg/ml in 0.1 M sodium acetate buffer, pH 4.5 with pepsin (Worthington Biochemical Corp., Free Hold, N.J.) at an enzyme substrate ratio of 1:100. In one experiment, aliquots were removed from the reaction mixture at 1, 3, 5, 7, 9 and 16 hours; in another, all reactions were stopped in 6 hours. To stop the reaction, solid Tris base was added to bring the pH to 8.0. The samples were frozen at −70° until analysis.

High pressure liquid chromatography was performed to judge the size of PEG-conjugates before and after enzymatic digestion. For this the FPLC system (Pharmacia-LKB, Piscataway, N.J.) was used, equipped with a Superose 12 Column. Fractions of native IgG, PEG conjugated immunoglobulins, or enzymatically-digested native or PEG conjugated immunoglobulins were loaded onto the column, equilibrated and run in 0.05 M Na phosphate buffer pH 7.3. The flow rate was set at 0.3 ml/minute, and fractions of 0.5 ml were collected.

FIG. 2 shows the results for trypsin digestion of native IgG or PEG IgG conjugates A, B, D, E, F50 and F100. While native IgG was fragmented into two major peaks, conjugate A remained more intact, and conjugate B remained almost totally intact after this procedure. Conjugates D, E F50, and F100 displayed only one major peak and were found virtually impervious to trypsin.

FIG. 3 shows results for chymotrypsin digestion of PEG-conjugates in comparison to native IgG. This enzyme fragmented IgG into several fragments; PEG-IgG conjugates were less susceptible to the actions of this enzyme. Examples are conjugates D, E and F50 shown in FIG. 3.

Similarly, after digestion of IgG or PEG-IgG conjugates by pepsin, PEG-IgG conjugates were found to remain more intact, with less of the main cleavage product, the F(ab) '2 segment being formed even after 10 hours of exposure to the enzyme. FIG. 3 shows data for native IgG, and the F100 and C conjugates. While some cleavage products formed after 6 hours of digestion for conjugates F100 and C, the amounts were half that of the native IgG.

We conclude that to achieve significant stability to enzymatic attack, about 7% of the lysines are desirably coupled; however above 27% of coupling of PEG, loss of antibody binding appears. Using the cyanuric chloride method, more antibody activity is lost than when a more gentle method is used. We find that using PEG 8000 as opposed to PEG 2000 results in similar biologic compounds, but that use of PEG 8000 results in greater blockage of conjugate binding to Fc receptors, and reduced fixation of complement C3, possibly due to the resistance of these compounds to aggregation.

TABLE 1

| USE OF IMMUNOGLOBULIN ORALLY | | | |
|---|---|---|---|
| IVGG Sandoglobulin(1) | 50 mg/kg × 4 doses a day | BMT recipients | IgG in stool median 40 mg/dl |
| Human gammaglobulin (IMGG)(2) | 500 mg × 4 day placebo | Low birth weight infants; rotavirus infections | Reduced rotavirus excretion and diarrhea |
| IVGG Cutter(3) | 150 mg/kg 1–10 doses | Immunodeficient subjects; rotavirus infections | (Clinical efficacy not studied) $I^{125}$ recovery = 50%, rotavirus antibody recovered |
| IVGG Cutter Lab(4) | 158 mg to 1120 mg/24 h × 5 days | Survival studies in low birth weight infants | 250–680 mg/dl (maximum) in stools of infants fed more Ig. No tetanus |

TABLE 1-continued

USE OF IMMUNOGLOBULIN ORALLY

| IgG-IgA preparation (Igabulin)[5] | 650 mg/Ig/ OD in 3 or 4 doses | Low birth weight infants | antibody found Reduced necrotizing entero-colitis; IgA in stool 1–10 mg/ dry wt. feces |
| IVGG Sandoglobulin[6] | 50 mg/kg 100 × 30 days | BMT recipients | Deceased hemorrhagic gastroenteritis |

[1] Copeland, EA. Bechtel, Featheringham NC, Grose NM, Sedmak D, Kapoor N, Tutschka P. Oral administration of IgG in marrow transplant recipient. Drug Intelligence and Clinical Pharmacology. 22:912, 1988.

[2] Barnes GL, Doyle LW, Hewson PH, Knoches AML, McLellan JA, Kitchen WH, and Bishop RF. A randomized trial of oral gammaglobulin in low-birth-weight infants infected with rotavirus. Lancet 1:1371:3, 1982.

[3] Losonsky GA, Johnson JP, Winkelstein JA, Yolken RH. Oral administration of human serum immunoglobulin in immuno-deficient patients with viral gastroenteritis. J. Clin. Invest. 2362:2367, 1985.

[4] Blum PM, Phelps DL, Ank BJ, Krantman HJ, Stiehm ER. Survival of oral human immune serum globulin in the gastro-intestinal tact of low-birth-weight infants. Pediatr. Res. 15:1256–60, 1981.

[5] Eibl MM, Wolf HM, Furnkranz H, and Rosenkranz A. Prevention of necrotizing entero-colitis in low-birth-weight infants by IgA-IgG feeding. New Eng. J. Med. 318, 1–7, 1988.

[6] Tutschka PJ. Infectious and immunodeficiency in bone marrow transplantation. Pediatr. Infect. Dis. J. 7:522–529, 1988.

TABLE 2

| Preparation | PEG | Method | Coupling Ratio | % Fluorescence | % Amines Coupled |
|---|---|---|---|---|---|
| A | 8000 | Carbonyl diimidazole | 1:10 | 95.6 | 4.4 |
| B | 8000 | Carbonyl diimidazole | 1:100 | 93.2 | 6.8 |
| C | 8000 | Carbonyl diimidazole | 1:1000 | 72.8 | 27.2 |
| D | 2000 | Carbonyl diimidazole | 1:5 | 91.3 | 8.7 |
| E | 2000 | Carbonyl diimidazole | 1:10 | 86.9 | 13.1 |
| F50 | 2000 | Carbonyl diimidazole | 1:50 | 86.0 | 14.0 |
| F100 | 2000 | Carbonyl diimidazole | 1:100 | 84.9 | 15.1 |
| F1000 | 2000 | Carbonyl diimidazole | 1:1000 | 83.9 | 16.1 |
| J | 2000 | Cyanuric chloride | 1:5 | 96.1 | 3.1 |
| K | 2000 | Cyanuric chloride | 1:10 | 93.6 | 6.4 |
| L | 2000 | Cyanuric chloride | 1:50 | 92.7 | 7.3 |
| I | 2000 | Cyanuric chloride | 1:288 | ND | ND |

TABLE 3

ANTIBODY BINDING I
Absorbence 405 nm

| | Tetanus | Ovalbumin | Bovine Immunoglobulin | Casein | Mumps |
|---|---|---|---|---|---|
| IgG Control | 1.493 | 0.713 | 0.713 | 0.725 | 0.318 |
| Conjugates: | | | | | |
| A | 1.510 | 0.625 | 0.946 | 0.640 | 0.308 |
| B | 1.337 | 0.778 | 0.972 | 0.604 | 0.376 |
| C | 0.838 | 0.521 | 0.630 | 0.172 | 0.164 |
| D | 1.715 | 0.440 | 0.476 | 0.631 | 0.268 |
| E | 1.814 | 0.676 | 0.648 | 0.572 | 0.283 |
| F-50 | 0.838 | 0.662 | 0.785 | 0.592 | 0.455 |
| F-100 | 1.655 | 0.514 | 0.518 | 0.606 | 0.318 |
| F-1000 | 1.884 | 0.676 | 0.775 | 0.509 | 0.389 |
| J | 1.706 | 0.777 | 0.764 | 0.746 | 0.314 |
| K | 0.820 | 0.760 | 0.700 | 0.550 | ND |
| L | 0.830 | 0.750 | 0.650 | 0.361 | ND |
| I | 0.146 | 0.112 | 0.128 | 0.139 | ND |
| PBS | 0.059 | 0.013 | 0.407 | 0.038 | 0.048 |

*Antigens used for coating microtiter plates at 10 μg/ml, except for mumps where whole vaccine was diluted to provide 100 units/ml.
**Data are expressed as OD Units at Absorbance 405 nm.

TABLE 4

ANTIBODY BINDING II*

| IgG Compound | Rubella | Varicella zoster | Herpes Simplex I | Cytomegalo Virus | Toxoplasma |
|---|---|---|---|---|---|
| PEG-IgG Conjugates | | | | | |
| A | 58.6 | 108.5 | 43.5 | 52.6 | 48.9 |
| B | 52.6 | 110.7 | 43.6 | 46.5 | 70.1 |
| C | 42.0 | 97.1 | 26.7 | 35.5 | 46.0 |
| D | 62.5 | 121.5 | 48.4 | 55.4 | 53.4 |
| E | 62.1 | 122.0 | 42.8 | 50.1 | 47.8 |
| F50 | 61.1 | 110.7 | 43.3 | 50.7 | 48.3 |
| F100 | 56.9 | ND | 45.3 | 41.7 | 43.8 |
| J | 59.1 | 92.0 | 52.1 | 61.9 | 80.3 |
| K | 56.4 | 71.0 | 37.9 | 47.4 | 55.0 |
| L | 43.6 | 66.0 | 22.7 | 29.7 | 39.1 |
| I | ND | 0.6 | 0.6 | 4.5 | 1.1 |
| Negative Controls: | 2.77 | 1.80 | 0.28 | 3.86 | 13.0 |
| Positive IgG Control: | >15 | >20 | >20 | >23 | >45 |

Data given in ELISA Index units per ml (EU/ml), where the known EU of the calibrator positive control ÷ experimental Absorbance 405 nm of the calibrator × Absorbance 405 nm of test sample = EU/ml of test sample. All samples were tested at the same concentration.

TABLE 5

BINDING OF PEG-Ig TO Fc RECEPTORS ON U937 MACROPHAGE CELL LINE

| Experiments | Sample Tested | Quandrant percent positive | Percent of control fluorescence | Percent inhibition |
|---|---|---|---|---|
| I. | FITC-control IgG | 5.17 | | |
| | PEG-IgG-A | 96.00 | 100 | 0 |
| | PEG-IgG-B | 81.00 | 84 | 16 |
| | PEG-IgG-C | 69.00 | 72 | 28 |
| | | 68.00 | 45 | 55 |
| II. | FITC-control | 3.10 | | |
| | IgG | 92.46 | 100 | 0 |
| | PEG-IgG-D | 80.90 | 88 | 12 |
| | PEG-IgG-E | 84.34 | 91 | 9 |
| III. | FITC-control | 8.80 | | |
| | IgG | 89.64 | 0 | 0 |
| | IgG-PEG-F100 | 76.68 | 86 | 14 |
| | IgG-PEG-F1000 | 70.73 | 79 | 21 |
| IV. | FITC-control | 4.3 | | |
| | IgG | 90.16 | 100 | 0 |
| | PEG-IgG-J | 85.77 | 95 | 5 |
| | PEG-IgG-K | 79.83 | 89 | 11 |
| | PEG-IgG-L | 72.06 | 80 | 20 |

*FITC Control = fluorescein isothiocyanate conjugated antibody to hman IgG F(ab)'2 was added alone.

TABLE 6

COMPLEMENT FIXATION

| IgG Compound* | Absorbance 405 nm | % of IgG control |
|---|---|---|
| Native IgG | 0.270 | 100 |
| Conjugates: | | |
| A | 0.270 | 100 |
| B | 0.229 | 85 |
| C | 0.190 | 70 |
| D | 0.234 | 56 |
| F50 | 0.127 | 47 |
| F100 | 0.097 | 36 |
| J | 0.097 | 49 |
| PBS | 0.000 | 0.0 |

IgG and IgG-PEG conjugates tested at equal concentrations (22.5 µg/ml); similar data were found for other concentrations of IgG tested, 225 µg/ml and 2.25 µg/ml)

TABLE 7

BINDING OF A SECOND ANTIBODY TO PEG-IgG CONJUGATES

| IgG Compound | % of Control IgG Bound to ELISA Plate* | % of Control IgG Detected in Solution** |
|---|---|---|
| Native IgG | 100 | 100 |
| Conjugates: | | |
| A | 100 | 95 |
| B | 87 | 100 |
| C | 63 | 39 |
| D | 100 | 95 |
| E | 100 | 100 |
| F100 | 93 | 100 |
| F1000 | 86 | 100 |
| J | 100 | 100 |
| K | 96 | 100 |
| L | 95 | 100 |

*Percent of control IgG solution bound to wells of microtiter plates; all solutions at 10 µg/ml concentration.
**Percent of control IgG solution detected by nephelometer; all solutions at 0.5 mg/ml.

We claim:

1. An oral pharmaceutical composition comprising an immunologically active polyethylene glycol serum immunoglobulin conjugate and a pharmaceutically acceptable oral carrier, wherein the oral carrier includes at least one ingredient selected from the group consisting of excipients used in the formulation of tablets and capsules, controlled release or protective coating materials used in the preparation of oral pharmaceutical preparation, flavorants and sweeteners.

2. An oral pharmaceutical composition according to claim 1, wherein the serum immunoglobulin in the conjugate is immunoglobulin G.

3. An oral pharmaceutical composition according to claim 1, wherein the serum immunoglobulin in the conjugate is immunoglobulin A.

4. A composition according to claim 2 or 3, wherein from 6.0% to 27% of the available lysines of the immunoglobulin are modified by the polyethylene glycol.

5. A composition according to claim 1, wherein the composition is formed into a capsule or a tablet.

6. A composition according to claim 1, wherein the oral carrier is an aqueous liquid containing a flavorant component.

7. A composition according to claim 2 or 3, wherein the oral carrier is an aqueous liquid containing a flavorant component.

8. A composition according to claim 2 or 3, wherein the conjugate is formed by reacting carbonyldiimidazole activated polyethylene glycol with immunoglobulin at a molar ratio of from 1:5 to 1:1000.

9. A composition according to claim 2 or 3, wherein the conjugate is formed by reacting cyanuric chloride activated polyethylene glycol with immunoglobulin at a molar ratio of 1:5 to 1:50.

10. A composition according to claim 6, wherein the oral carrier is milk, infant formula or fruit juice.

11. A composition according to claim 2 or 3 wherein the conjugate is formed by reacting succinyl succinamide activated polyethylene glycol with immunoglobulin at a molar ratio of 1:5 to 1:1000.

12. A method for reconstituting secretory immunity in a patient suffering from a secretory immune deficiency comprising orally administering an effective amount of a polyethylene glycol serum immunoglobulin conjugate to the patient.

13. A method according to claim 12, wherein the serum immunoglobulin in the conjugate is immunoglobulin A.

14. A method according to claim 12 wherein the serum immunoglobulin in the conjugate is immunoglobulin G.

15. A method according to claim 13 or 14, wherein from 6.0% to 27% of the available lysines of the immunoglobulin are modified by the polyethylene glycol.

16. A method according to claim 13 or 14, wherein the conjugate is administered in an amount of from 100 to 400 mg/kg body weight/day.

* * * * *